United States Patent [19]

Martel et al.

[11] 4,447,637
[45] May 8, 1984

[54] EPIMERIZATION OF TRANS CHRYSANTHEMATES

[75] Inventors: Jacques Martel, Bondy; Jean Buendia, Le Perreux sur Marne; Jeanine Nierat, Luzernes, all of France

[73] Assignee: Roussel Uclaf, Paris, France

[21] Appl. No.: 347,278

[22] Filed: Feb. 9, 1982

[30] Foreign Application Priority Data

Feb. 13, 1981 [FR] France .................... 81 02828

[51] Int. Cl.³ .................... C07C 69/74; C07C 61/18
[52] U.S. Cl. .................... 560/124; 562/506; 556/446
[58] Field of Search .................... 562/506; 560/124

[56] References Cited

U.S. PATENT DOCUMENTS

| 3,786,070 | 1/1974 | Martel et al. ............. 562/506 X |
| 3,836,568 | 9/1974 | Higo et al. ............. 560/124 |
| 3,931,280 | 6/1976 | Nagase et al. ............. 560/124 |
| 3,989,654 | 11/1976 | Honda et al. ............. 562/506 |
| 4,166,064 | 8/1979 | Kondo et al. ............. 560/124 X |
| 4,233,129 | 11/1980 | Franck-Neumann et al. ..... 560/124 X |
| 4,299,973 | 11/1981 | Franck-Neumann et al. ..... 560/124 |
| 4,306,077 | 12/1981 | Leigh ............. 562/506 X |

FOREIGN PATENT DOCUMENTS 43143 1/1982 European Pat. Off. ............. 560/124

Primary Examiner—Paul F. Shaver
Attorney, Agent, or Firm—Muserlian, Bierman, Bierman & Peroff

[57] ABSTRACT

A novel process for the epimerization of alkyl trans chrysanthemates comprising reacting at a low temperature in an anhydrous organic solvent an alkyl trans chrysanthemate of the formula

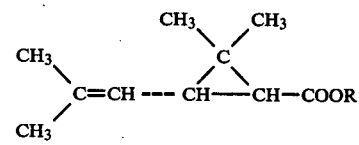

of the 1S, trans or 1R, trans configuration wherein R is alkyl of 1 to 6 carbon atoms with a strong alkali metal base to obtain a compound of the formula

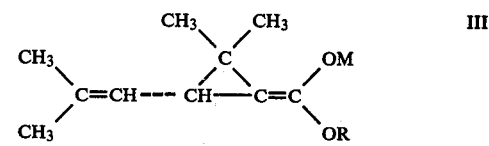

wherein R has the above definition and M is an alkali metal, reacting the latter compound with a reactant of the formula

Y—A wherein A is selected from the group consisting of chlorine, bromine, iodine and anion derived from a hydrogen acid and Y is an organic radical capable of forming a ketal of a ketene to obtain a compound of the formula

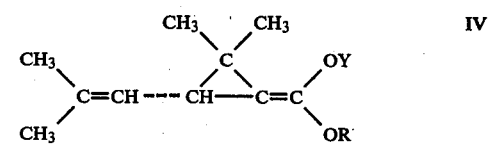

reacting the latter at a low temperature in an anhydrous organic solvent with a proton donor to obtain a mixture of the corresponding alkyl cis chrysanthemate and alkyl trans chrysanthemate and recovering the cis chrysanthemic acid of the formula

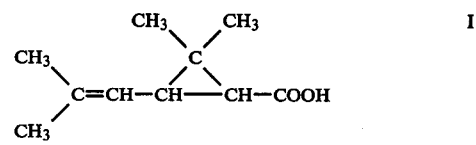

with the 1R, cis or 1S, cis configuration.

9 Claims, No Drawings

EPIMERIZATION OF TRANS CHRYSANTHEMATES

STATE OF THE ART

Process are known for the epimerization of cis chrysanthemic acid of formula I with the 1R,cis or 1S,cis configuration to the corresponding trans chrysanthemic acid. It is known that the more thermodynamically stable form is the trans form and the equilibrium, depending on the operating conditions, is on the order of 90% of trans chrysanthemic acid and 10% of cis chrysanthemic acid. However, the compounds of the cis series are of a great commercial interest as it has been discovered that the esters of 1R,cis 2,2-dimethyl-3-(2,2-dihalovinyl)-cyclopropane-1-carboxylic acids have elevated insecticidal activity

OBJECTS OF THE INVENTION

It is an object of the invention to provide a novel process for the epimerization of alkyl trans chrysanthemates and especially alkyl 1S,trans chrysanthemates to alkyl 1R,cis chrysanthemate.

It is another object of the invention to provide novel intermediates.

These and other objects and advantages of the invention will become obvious from the following detailed description.

THE INVENTION

The novel process of the invention for the epimerization of alkyl trans chrysanthemate comprises reacting at a low temperature in an anhydrous organic solvent an alkyl trans chrysanthemate of the formula

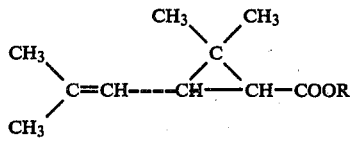

of the 1S,trans or 1R,trans configuration wherein R is alkyl of 1 to 6 carbon atoms with a strong alkali metal base to obtain a compound of the formula

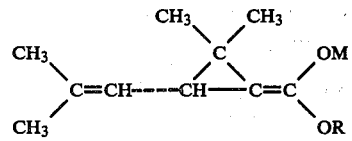

wherein R has the above definition and M is an alkali metal reacting the latter compound with a reactant of the formula

Y—A wherein A is selected from the group consisting of chlorine, bromine, iodine and anion derived from a hydrogen acid and Y is an organic radical capable of forming a ketal of a ketene to obtain a compound of the formula

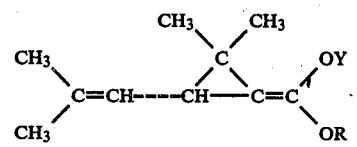

reacting the latter at a low temperature in an anhydrous organic solvent with a proton donor to obtain a mixture of the corresponding alkyl cis chrysanthemate and alkyl trans chrysanthemate. The alkyl ester of cis chrysanthemic acid is separed from the mixture then the said cis acid is isolated by known methods. The process is successful in spite of the grave difficulties due to the thermodynamic equilibrium in favor of the trans form.

The first step of the process of the invention is essentially characterized by reacting a strong base in an anhydrous medium with an alkyl trans chrysanthemate of formula II of 1S,trans or 1R,trans configuration to obtain an enolate of formula III.

The formation of the ketene ketal of formula IV from the enolate of formula III takes place without degradation only with certain reactants permitting the trans formation in a satisfactory manner. It is necessary to use a "hard" reactant alkylating oxygen in preference to carbon such as a derivative of the type.

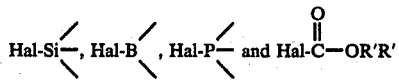

being alkyl of 1 to 6 carbon atoms leading to the formation of a O-silane, borate, phosphonate or carbonate derivative or to a derivative of the type $CH_3S-Si(CH_3)_3$,

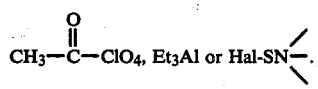

The following step of the process of the invention is essentially characterized in that the ketene of the ketal of formula IV as first formed is reacted in an anhydrous medium with a proton donor which attacks the more free side of the molecule and leads to the desired epimerization. The success of this epimerization step is surprising.

It doesn't take place, in effect, in a satisfactory manner in the presence of any proton donor and the proton donors must be sufficiently voluminous to attack the molecule on its least-encumbered face leading to the formation of the cis derivative and the reaction is effected at a low temperature to realize a kinetic protonation.

It is understood that the various reactions of the process of the invention are effected in an anhydrous media for formation of the enolate, the attack by the Y—A reactant and even the attack by the proton donor. Finally, the success of the process requires that the operating conditions be well defined for the choice of the O-alkylating reactant for the choice of the proton donor.

The variation of the process of the invention is essentially characterized in that the proton donor is reacted directly with the enolate of formula III to obtain the cis derivative. Analogous conditions discussed above for the basic process apply to the variation as well. Only well defined operating conditions permit obtaining an interesting percentage of epimerization.

The process of the invention leads to yields of the cis derivatives up to 70% which is very remote from the previously indicated thermodynamic equilibrium. The transformation into the alkyl cis chrysanthemate is not complete and the desired cis chrysanthemic acid can be recovered from the resulting mixtures by known procedures. For example, the mixture of esters may be saponified to obtain a mixture of (1S,trans) and (1R,cis) chrysanthemic acids, then forming a salt of L (+) threo 1-p-nitrophenyl-2-dimethylamino-propane-1,3-diol of the (1S,trans) acid which is removed by filtration and acidifying the filtrate to obtain the desired (1R,cis) chrysanthemic acid.

The process of the invention is particularly of interest for the transformation of 1S,trans chrysanthemic acid into 1R,cis chrysanthemic acid under advantageous conditions with readily available reactants. This transformation proves to be useful since 1S,trans chrysanthemic acid is obtained in the resolution of dl cis trans chrysanthemic acid obtained synthetically leading by oxidation and then by the Wittig reaction with the resulting aldehyde to (1S,trans) 2,2-dimethyl-3-[2,2-dihalovinyl]-cyclopropane-1-carboxylic acids whose esters do not have interesting insecticidal activity. Now due to the process of the invention, the previously unusable (1S,trans) chrysanthemic acid from the resolution of dl cis trans chrysanthemic acids may be subjected to an analogous set of reactions to obtain (1R,cis) 2,2-dimethyl-3-(2,2-dihalovinyl)-cyclopropane-1-carboxylic acids whose esters do have interesting insecticidal properties.

In the compounds of formulae II, III and IV, R may be methyl, ethyl, n-propyl, isopropyl or linear or branched butyl, pentyl or hexyl. M may be potassium, sodium or lithium. In the reactant Y—A, Y may be dialkoxyphosphonyl or dialkylboride of 1 to 6 alkyl carbon atoms, ethylenedioxyboride, dimethyltert-butylsilyl or trimethylsilyl.

In the process of the invention or its variant, R is preferably methyl or ethyl and the strong alkali metal base is lithium diisopropylamide and the low temperature for the reactions is between −20° and 70° C. The organic solvent for the reactions is selected from ethers, aromatic hydrocarbons and mixtures thereof.

The preferred proton donors are selected from the group consisting of 2,4-dimethyl-6-tert.-butyl-phenol, collidine hydrochloride, acridine hydrochloride, diisopropylamine hydrochloride, isopropylethylamine hydrochloride, hexamethylenetetramine hydrochloride, collidine hydroiodide, anhydrous silica, a mixture of anhydrous silica and anhydrous hydrogen chloride, ethyl acetylacetate, 3,3,6,9,9-pentamethyl-2,10-diazabicyclo-[4,4,0]-1-decene hydrochloride and water.

The compounds of formula IV are novel intermediates and are a part of the invention.

In the following examples there are described several preferred embodiments to illustrate the invention. However, it should be understood that the invention is not intended to be limited to the specific embodiments.

EXAMPLE 1

(1R,cis) chrysanthemic acid

STEP A: Mixture of methyl (1R,cis) chrysanthemate and methyl (1S,trans) chrysanthemate 4.1 ml of a solution of 1.95 mmole of butyllithium per ml of cyclohexane were added at −10° C. to a solution of 1.2 ml of diisopropylamine in 5 ml of anhydrous tetrahydrofuran and the mixture was stirred at −10° C. for 20 minutes and was then cooled to −50° C. A solution of 1 g of methyl (1S,trans) chrysanthemate in 5 ml of anhydrous tetrahydrofuran was added to the mixture at −50° C. and the resulting mixture was stirred at −50° C. for 30 minutes after which 3 ml of trimethylsilyl chloride were added thereto. The mixture was stirred at −50° C. for 2½ hours and 2.5 g of collidine hydrochloride were added thereto. The mixture was stirred at −5° C. for 4 hours and the temperature was allowed to rise slowly to 20° C. The mixture was poured into a concentrated monosodium phosphate solution and the mixture was extracted with ether. The ether phase was dried and evaporated to dryness under reduced pressure. The residue was chromatographed over silica gel and was eluted with a 1-1 benzene-cyclohexane mixture to obtain 0.720 g of a mixture of methyl (1R,cis) chrysanthemate and methyl (1S,trans) chrysanthemate. It was determined by vapor phase chromatography that the mixture consisted of 56% of the (1R,cis) ester and 42% of the (1S,trans) ester and 1.5% and 0.5% of two impurities of indeterminate structure.

NMR Spectrum (deuterochloroform):

(a) trans structure

Peaks at 1.12–1.23 ppm (hydrogens of geminal methyls); at 3.5 ppm (hydrogens of

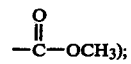

at 4.83–4.97 ppm (hydrogens of ethylenic double bond).

(b) cis structure

Peaks at 1.18–1.22 ppm (hydrogens of geminal methyls); at 3.5 ppm (hydrogens of

at 5.35–5.48 ppm (hydrogens of ethylenic double bond).

STEP B: Mixture of (1R,cis) chrysanthemic acid and 1S,trans chrysanthemic acid

A solution of 100 ml of methanol and 60 ml of sodium hydroxide solution (24 g of NaOH) after degassification was refluxed under nitrogen for 15 minutes and then 0.720 g of the mixture of Step A in 1.2 ml of the degassed sodium hydroxide solution was added thereto. The mixture was refluxed under an inert atmosphere for 3 hours and was washed and admixed with 0.7 ml of water. The methanol was distilled off under reduced pressure and the mixture was adjusted to a pH of 2 by addition of aqueous hydrochloric acid while keeping the temperature below 25° C. The mixture was extracted with methylene chloride and the organic phase was evaporated to dryness under reduced pressure to obtain 0.657 g of a 43–57 mixture of (1R,cis) chrysanthemic acid and 1S,trans chrysanthemic acid which was used as is for the next step.

STEP C: (1R,cis) chrysanthemic acid 0.880 g of L (+) threo 1-p-nitrophenyl-2-dimethylamino-propane-1,3-diol were progressively added with stirring to a solution of 0.657 g of the product of Step B in 0.3 ml of methanol and 1.8 ml of isopropyl ether and the mixture was heated over 15 minutes to reflux under an inert atmosphere and reflux was continued for 15 minutes. The mixture was cooled to 0° C. and stirred at 0° C. for 2 hours and was filtered to remove L (+) threo 1-p-nitrophenyl-2-dimethylamino-propane-1,3-diol salt of (1S,trans) chrysanthemic acid. The filter was washed with a 85-15 isopropyl ether-methanol mixture and the combined filtrates were slowly acidified below 25° C. to congo red acidity with aqueous 0.5 M/l of hydrochloric acid. The decanted aqueous phase was extracted with isopropyl ether and the organic phase was washed with water and evaporated to dryness under reduced pressure to obtain 0.308 g of (1R,cis) chrysanthemic acid.

EXAMPLE 2

Mixture of methyl (1R,cis) chrysanthemate and methyl (1S,trans) chrysanthemate 3.55 ml of a solution of 1.85 mmols/ml of butyllithium in cyclohexane were added at −10° C. to a solution of 1 ml of diisopropylamine in 5 ml of anhydrous ether and the mixture was stirred at −10° C. for 20 minutes. Then, a solution of 1 g of methyl (1S,trans) chrysanthemate in 5 ml of ether were added thereto at −40° C. and the mixture was stirred at −40° C. for one hour. 2 ml of trimethylsilyl chloride were added to the mixture which was stirred at −40° C. for 2½ hours. 2.5 g of collidine hydrochloride were added to the mixture which was then stirred at −40° C. for 4 hours. The temperature was allowed to slowly rise to 20° C. and the mixture was poured into a saturated aqueous monosodium phosphate solution. The mixture was extracted with ether and the organic phase was evaporated to dryness under reduced pressure. The residue was chromatographed over silica gel and eluted with a 1-1 benzene-cyclohexane mixture to obtain 0.581 g of a mixture of methyl (1R,cis) chrysanthemate and methyl (1S,trans) chrysanthemate. Vapor phase chromatography showed the mixture consisted of 74.7% of the (1R,cis) ester and 25.3% of the (1S,trans) ester.

EXAMPLE 3

Mixture of methyl (1R,cis) chrysanthemate and methyl (1S,trans) chrysanthemate 3.85 ml of a solution of 1.7 mmoles per ml of butyllithium in cyclohexane were added at −10° C. to a solution of 1 ml of diisopropylamine in 5 ml of anhydrous tetrahydrofuran and the mixture was stirred at −10° C. for 20 minutes. A solution of 1 g of methyl (1S,trans) chrysanthemate in 5 ml of tetrahydrofuran were added thereto at −40° C. and the mixture was stirred at −40° C. for one hour. 3 ml of trimethylsilyl chloride were added to the mixture which was stirred at −40° C. for 2½ hours after which 2.5 g of 3,3,6,9,9-pentamethyl-2,10-diazabicyclo [4,4,0]-1-decane hydrochloride were added thereto. The mixture was stirred at −40° C. for 4 hours and was then slowly allowed to rise to 20° C. The mixture was poured into aqueous saturated monosodium phosphate solution and the mixture was extracted with ether. The ether phase was evaporated to dryness under reduced pressure and the residue was chromatographed over silica gel. Elution with a 1-1 benzene-cyclohexane mixture yielded 0.775 g of a mixture of methyl (1R,cis) chrysanthemate and methyl (1S,trans) chrysanthemate. Vapor phase chromatography showed that the mixture was 63% of the (1R,cis) ester and 37% of (1S,trans) ester.

EXAMPLE 4

4.45 ml of a solution of 1.8 mmoles per ml of butyllithium in cyclohexane were added at −10° C. to a solution of 1.2 ml of diisopropylamine in 5 ml of anhydrous ether and after stirring the mixture at −10° C. for 15 minutes, a solution of 1 g of methyl (1S,trans) chrysanthemate in 5 ml of anhydrous ether were added thereto at −50° C. The mixture was stirred at −50° C. for 30 minutes and then 3 ml of trimethylsilyl chloride were added thereto. The mixture was stirred at −50° C. for 2½ hours and 2.5 g of collidine hydrochloride were added thereto. The mixture was stirred at −50° C. for 3 hours and the temperature was allowed to slowly rise to 20° C. The reaction mixture was poured into an aqueous saturated monosodium phosphate solution and was extracted with ether. The ether phase was evaporated to dryness under reduced pressure and the residue was chromatographed over silica gel. Elution with a 1-1 benzene-cyclohexane mixture yielded 0.760 g of a mixture of methyl (1R,cis) chrysanthemate and methyl (1S,trans) chrysanthemate. Vapor phase chromatography showed the mixture contained 63% of the (1R,cis) ester and 37% of the (1S,trans) ester.

EXAMPLE 5

4.1 ml of a solution of 1.95 mmoles per ml of butyllithium in cyclohexane were added at −10° C. to a solution of 1.2 ml of diisopropylamine in 5 ml of anhydrous ether and the mixture was stirred at −10° C. for 20 minutes. A solution of methyl (1S,trans) chrysanthemate in 5 ml of ether was added thereto at −40° C. and the mixture was stirred at −40° C. for 30 minutes. Then, 3 ml of of trimethylsilyl chloride were added thereto and the mixture was stirred at −40° C. for 2½ hours. 2.5 g of collidine hydrochloride were added to the mixture which was stirred at −30° C. for 15 hours and was then poured into aqueous saturated monosodium phosphate solution. The mixture was extracted with ether and the organic phase was evaporated to dryness under reduced pressure. The residue was chromatographed over silica gel and was eluted with a 1-1 benzene-cyclohexane mixture to obtain 0.600 g of a mixture of methyl (1R,cis) chrysanthemate and methyl (1S,trans) chrysanthemate. Vapor phase chromatography showed that the mixture contained 78.1% of the (1R,cis) ester and 21.9% of the (1S,trans) ester.

EXAMPLE 6

4.7 ml of a solution of 1.7 mmole per ml of butyllithium in cyclohexane were added at −10° C. to a solution of 1.2 ml of diisopropylamine in 5 ml of anhydrous tetrahydrofuran and the mixture was stirred at −10° C. for 30 minutes. A solution of 1 g of methyl (1S,trans) chrysanthemate in 5 ml of tetrahydrofuran was added to the mixture at −40° C. and the mixture was stirred at −40° C. for 30 minutes. Then, 3 ml of trimethylsilyl chloride were added to the mixture which was stirred at −40° C. for 2 hours and was poured into ice. The mixture was extracted with ether and the organic phase was evaporated to dryness under reduced pressure. The residue was chromatographed over silica gel and was eluted with a 1-1 benzene-cyclohexane mixture to obtain 0.852 g of a mixture of methyl (1R,cis) chrysanthemate and methyl (1S,trans) chrysanthemate. Vapor phase chromatography showed the mixture contained 56% of the (1R,cis) ester and 44% of the (1S,trans) ester.

EXAMPLE 7

The procedure of Example 6 was repeated except after 2 hours of stirring at −40° C., 1.6 g of collidine hydrochloride were added and the mixture was stirred at −40° C. for 60 hours. Then the mixture was poured into aqueous saturated monosodium phosphate solution and the mixture was extracted with ether. The organic phase was evaporated to dryness under reduced pressure and the residue was chromatographed over silica gel. Elution with a 1-1 benzene-cyclohexane mixture yielded 0.569 g of a mixture of methyl 1R,cis chrysanthemate and methyl 1S,trans chrysanthemate. Vapor phase chromatography showed that the mixture consisted of 69% of the 1R,cis isomer and 31% of the 1S,trans isomer.

EXAMPLE 8

2.35 ml of a 1.7 mmole/ml of butyllithium in cyclohexane were added at −10° C. to a mixture of 0.6 ml of diisopropylamine and 5 ml of anhydrous tetrahydrofuran and the mixture was stirred at −10° C. for 30 minutes. A solution of 0.5 g of methyl 1S,trans chrysanthemate in 5 ml of tetrahydrofuran was added to the mixture at −40° C. and the mixture was stirred for 30 minutes at −40° C. Then, 2.8 g of 3,3,6,9,9-penta-methyl-2,10-diazabicyclo [4,4,0]-1-decene hydrochloride were added to the mixture which was stirred at −40° C. for 60 hours and was poured into aqueous saturated monosodium phosphate solution. The mixture was extracted with ether and the organic phase was evaporated to dryness under reduced pressure. The residue was chromatographed over silica gel and was eluted with a 1-1 benzene-cyclohexane mixture to obtain 0.419 g of a mixture of 45% of methyl 1R,cis chrysanthemate and 55% of methyl 1S,trans chrysanthemate as determined by vapor phase chromatography.

EXAMPLE 9

3.65 ml of a 1.5 mmole/ml of butyllithium in cyclohexane were added at −10° C. to a solution of 0.8 ml of diisopropylamine in 3.5 ml of anhydrous tetrahydrofuran and the mixture was stirred at −10° C. for 15 minutes. A solution of 1 g of methyl 1S,trans chrysanthemate in 5 ml of tetrahydrofuran was added at −20° C. and the mixture was stirred at −20° C. for 3 hours. 2.8 g of 3,3,6,9,9-pentamethyl-2,10-diazabicyclo [4,4,0]-1-decene hydrochloride were added to the mixture which was then stirred at −20° C. for 40 hours and was poured into aqueous saturated monosodium phosphate solution. The mixture was extracted with ether and the organic phase was evaporated to dryness. The residue was chromatographed over silica gel and was eluted with a 1-1 benzene-cyclohexane mixture to obtain 0.778 g of a mixture which was determined by vapor phase chromatography to be 55% of methyl 1R,cis chrysanthemate and 45% of methyl 1S,trans chrysanthemate.

EXAMPLE 10

2.15 ml of a solution of 1.9 mmoles per ml of butyllithium in cyclohexane were added at −10° C. to a solution of 0.56 ml of diisopropylamine in 6 ml of anhydrous tetrahydrofuran and the mixture was stirred at −10° C. for 20 minutes. A solution of 0.5 g of methyl 1S,trans chrysanthemate in 5 ml of tetrahydrofuran were added to the mixture at −20° C. which was then stirred at −20° C. for 90 minutes and was poured into a solution of 1.35 g of 2,6-tert.-butyl-4-methyl-phenol in 10 ml of anhydrous tetrahydrofuran previously cooled to −20° C. The mixture was stirred at −20° C. for 20 hours and was poured into aqueous saturated monosodium phosphate solution. The mixture was extracted with ether and the organic phase was evaporated to dryness under reduced pressure. The residue was chromatographed over silica gel and was eluted with a 1-1 benzene-cyclohexane mixture to obtain 0.463 g of a mixture which was determined by vapor phase chromatography to be 42% of methyl 1R,cis chrysanthemate and 58% of methyl 1S,trans chrysanthemate.

EXAMPLE 11

2.15 ml of a solution of 19 mmoles per ml of butyllithium in cyclohexane were added at −10° C. to a solution of 0.56 ml of diisopropylamine in 6 ml of anhydrous tetrahydrofuran and the mixture was stirred at −10° C. for 20 minutes. A solution of 0.5 g of methyl 1S,trans chrysanthemate in 5 ml of tetrahydrofuran was added at −20° C. to the mixture which was then stirred at −20° C. for 90 minutes and was poured into a suspension of 1.1 g of diisopropylamine hydrochloride in 10 ml of anhydrous tetrahydrofuran. The mixture was stirred at −20° C. for 20 hours and was poured into aqueous saturated monosodium phosphate solution. The mixture was extracted with ether and the organic phase was evaporated to dryness under reduced pressure. The residue was chromatographed over silica gel and was eluted with a 1-1 benzene-cyclohexane mixture to obtain 0.373 mg of a mixture which was determined by vapor phase chromatography to be 40% of methyl 1R,cis chrysanthemate and 60% of methyl 1S,trans chrysanthemate.

EXAMPLE 12

3.05 ml of a solution of 1.8 mmole per ml of butyllithium in cyclohexane were added at −15° C. to a solution of 0.77 ml of diisopropylamine in 7 ml of anhydrous tetrahydrofuran and the mixture was stirred at −15° C. for 15 minutes. A solution of 1 g of methyl 1S,trans chrysanthemate in 10 ml of tetrahydrofuran was added at −25° C. to the mixture which was then stirred at −20° C. for 3 hours. 0.954 g of collidine hydrochloride were added to the mixture which was stirred at −20° C. for 18 hours and was then poured into an aqueous saturated monosodium phosphate solution. The mixture was extracted with ether and the organic phase was evaporated to dryness under reduced pressure. The residue was chromatographed over silica gel and was eluted with a 1-1 cyclohexane-benzene mixture to obtain 0.473 g of a mixture which was shown by vapor phase chromatography to be 51% of methyl 1R,cis chrysanthemate and 49% of methyl 1S,trans chrysanthemate.

EXAMPLE 13

2.15 ml of a solution of 1.9 mmole per ml of butyllithium in cyclohexane were added at −10° C. to a solution of 0.56 ml of diisopropylamine in 6 ml of anhydrous tetrahydrofuran and the mixture was stirred at −10° C. for 15 minutes. A solution of 0.5 g of methyl 1S,trans chrysanthemate in 5 ml of tetrahydrofuran were added at −20° C. to the mixture which was stirred at −20° C.

for 90 minutes and poured into a suspension of 1.4 g of acridine hydrochloride in 10 ml of anhydrous tetrahydrofuran previously cooled to −20° C. The mixture was stirred at −20° C. for 60 hours and was poured into aqueous saturated monosodium phosphate solution. The mixture was extracted with ether and the organic phase was evaporated to dryness under reduced pressure. The residue was chromatographed over silica gel and was eluted with a 1-1 benzene-cyclohexane mixture to obtain 0.407 g of a mixture which was determined by vapor phase chromatography to be 37% of methyl 1R,cis chrysanthemate and 63% of methyl 1S,trans chrysanthemate.

EXAMPLE 14

2.5 ml of a 1.6 M per liter of butyllithium in cyclohexane were added dropwise under a nitrogen atmosphere at −10° C. to a solution of 0.6 ml of diisopropylamine in 2.5 ml anhydrous tetrahydrofuran and the mixture was stirred at −10° C. for 15 minutes. A solution of 0.5 g of methyl 1S,trans chrysanthemate in 5 ml of tetrahydrofuran was added dropwise at −40° C. to the mixture which was stirred at −40° C. for 45 minutes. A solution of 750 mg of dimethyl tert.-butyl silyl chloride in 5 ml of anhydrous tetrahydrofuran was added dropwise at −40° C. to the mixture which was stirred at −40° C. for 2 hours and 5 ml of the mixture were poured into ice water. The mixture was extracted with ether and the organic phase was dried and evaporated to dryness. The residue was chromatographed over silica gel and was eluted with a 1-1 benzene-cyclohexane mixture to obtain 50 mg of a mixture of 36% of methyl 1R,cis chrysanthemate and 64% of methyl 1S,trans chrysanthemate.

The remainder of the solution was admixed with 800 mg of collidine hydrochloride and the mixture was stirred overnight at −40° C. and was poured into aqueous saturated monosodium phosphate solution. The mixture was extracted with ether and the ether phase was dried and evaporated to dryness under reduced pressure. The residue was chromatographed over silica gel and was eluted with a 1-1 benzene-cyclohexane mixture to obtain 175 mg of a mixture of 48% of methyl 1R,cis chrysanthemate and 52% of methyl 1S,trans chrysanthemate.

EXAMPLE 15

1 ml of a solution of 1.95 M per liter of butyllithium in cyclohexane was added dropwise under a nitrogen atmosphere at −10° C. to a solution of 1.2 ml of diisopropylamine in 5 ml of anhydrous tetrahydrofuran and the mixture was stirred at −10° C. for one hour. A solution of 1 g of methyl 1S,trans chrysanthemate in 5 ml of anhydrous tetrahydroufan was added at −40° C. to the mixture which was stirred at −40° C. for 30 minutes. A mixture of 1 g of 1-chloro-2,5-dioxoborolane in 5 ml of anhydrous tetrahydrofuran was added to the mixture at −40° C. which was then stirred at −40° C. for 2 hours. 5 ml of the solution were poured into ice and the mixture was extracted with ether. The organic phase was dried and evaporated to dryness under reduced pressure to obtain 443 mg of a raw oil containing 53.1% of methyl 1R,cis chrysanthemate and 46.9% of methyl 1S,trans chrysanthemate.

The remainder of the solution was admixed with 2 g of collidine hydrochloride and the mixture was stirred at −40° C. for 20 hours and was poured into aqueous saturated monosodium phosphate solution. The mixture was extracted with ether and the organic phase was dried and evaporated to dryness under reduced pressure to obtain 2.07 g of a raw oil containing 50.6% of methyl 1R,cis chrysanthemate and 49.4% of methyl 1S,trans chrysanthemate.

EXAMPLE 16

4.7 ml of a solution of 1.7 M per liter of butyllithium in cyclohexane were added dropwise under a nitrogen atmosphere at −15° C. to a solution of 1.2 ml of diisopropylamine in 5 ml of anhydrous tetrahydrofuran and the mixture was stirred at −15° C. for one hour. A solution of 1 g of methyl 1S,trans chrysanthemate in 5 ml of anhydrous tetrahydrofuran was added dropwise at −40° C. and the mixture was stirred at −40° C. for 30 minutes. Then 1.5 ml of dimethoxy chloroborane were added at −40° C. to the mixture which was stirred at −40° C. for one hour.

3 ml of the resulting solution were poured over ice and the mixture was extracted with ether. The organic phase was dried and evaporated to dryness under reduced pressure and the 162 mg of raw oil contained 53.3% of methyl 1R,cis chrysanthemate and 46.7% of methyl 1S,trans chrysanthemate.

The remainder of the solution was mixed with 2 g of collidine hydrochloride and the mixture was stirred at −40° C. for 16 hours and poured in an aqueous concentrated monosodium phosphate solution. The mixture was extracted with ether and the organic phase was dried and evaporated to dryness under reduced pressure to obtain 830 mg of a raw oil containing 53.5% of methyl 1R,cis chrysanthemate and 46.5% of methyl 1S,trans chrysanthemate.

EXAMPLE 17

4.7 ml of a 1.7 M/liter of butyllithium in cyclohexane were added dropwise under a nitrogen atmosphere at −10° C. to a solution of 1.2 ml of diisopropylamine in 5 ml of anhydrous tetrahydrofuran and the mixture was stirred at −10° C. for 30 minutes. A solution of 1 g of methyl 1S,trans chrysanthemate in 5 ml of anhydrous tetrahydrofuran was added dropwise at −40° C. to the mixture which was stirred for 30 minutes at −40° C. A solution of 1.72 g of diethyl chlorophosphate in 5 ml of tetrahydrofuran was added dropwise at −40° C. to the mixture which was stirred for 2 hours at −40° C.

5 ml of the solution were poured over ice water and the mixture was extracted with ether. The organic phase was dried and evaporated to dryness under reduced pressure to obtain 360 mg of a raw oil containing 38% of methyl 1R,cis chrysanthemate and 62% of methyl 1S,trans chrysanthemate.

The remainder of the solution was mixed with 1.5 g of collidine hydrochloride and the mixture was stirred at −40° C. for 16 hours and poured into an aqueous saturated monosodium phosphate solution. The mixture was extracted with ether and the organic phase was dried and evaporated to dryness under reduced pressure to obtain 951 mg of raw oil containing 43% of methyl 1R,cis chrysanthemate and 57% of methyl 1S,trans chrysanthemate.

Various modifications of the products and process of the invention may be made without departing from the spirit or scope thereof and it is to be understood that the invention is intended to be limited only as defined in the appended claims.

What we claim is:

1. A process for the epimerization of alkyl trans chrysanthemate comprising reacting at a low temperature in an anhydrous organic solvent an alkyl trans chrysanthemate of the formula

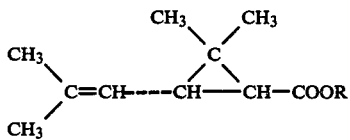

of the 1S,trans or 1R,trans configuration wherein R is alkyl of 1 to 6 carbon atoms with a strong alkali metal base to obtain a compound of the formula

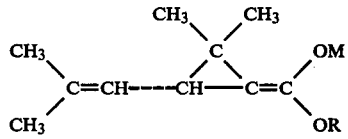

wherein R has the above definition and M is an alkali metal reacting the latter compound with a reactant of the formula

Y—A wherein A is selected from the group consisting of chlorine, bromine, iodine and anion derived from a hydrogen acid and Y is an organic radical capable of forming a ketal of a ketene to obtain a compound of the formula

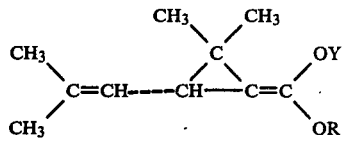

reacting the latter at a low temperature in an anhydrous organic solvent with a proton donor to obtain a mixture of the corresponding alkyl cis chrysanthemate and alkyl trans chrysanthemate.

2. The process of claim 1 wherein the alkyl trans chrysanthemate has the 1S,trans configuration.

3. The process of claim 1 wherein the compound of formula III is reacted with a proton donor at a low temperature in an anhydrous medium to obtain a mixture of alkyl trans chrysanthemate and alkyl cis chrysanthemate, separating the latter and recovering cis chrysanthemic acid.

4. The process of claim 1,2 or 3 wherein R is methyl or ethyl.

5. The process of claim 1 or 4 wherein the strong alkali metal base is lithium diisopropylamine.

6. The process of claim 1,4 or 5 wherein the low temperature is $-20°$ to $-70°$ C.

7. The process of claim 1 wherein the organic solvent is selected from the group consisting of ethers, aromatic hydrocarbons and mixtures thereof.

8. The process of claim 1 wherein the proton donor is selected from the group consisting of 2,4-dimethyl-6-tert.-butyl-phenol, collidine hydrochloride, acridine hydrochloride, diisopropylamine hydrochloride, isopropylethylamine hydrochloride, hexamethylenetetramine hydrochloride, collidine hydroiodide, anhydrous silica, a mixture of anhydrous silica and anhydrous hydrogen chloride, ethyl acetylacetate, 3,3,6,9,9-pentamethyl-2,10-diazabicyclo [4,4,0]-1-decene hydrochloride and water.

9. The process of claim 1,2 or 4 wherein Y is selected from the group consisting of dialkoxyphosphonyl, dialkylboride ethylenedioxy boride dimethyltert-butylsilyl and trimethylsilyl.

* * * * *